United States Patent
Gilutz et al.

(10) Patent No.: US 12,322,494 B2
(45) Date of Patent: Jun. 3, 2025

(54) SYSTEM AND METHOD FOR COGNITIVE TRAINING AND MONITORING

(71) Applicant: ACERAR LTD., Tel Aviv (IL)

(72) Inventors: Yael Gilutz, Tel Aviv (IL); Shai Granot, Herzelia (IL); Anna Izoutcheev, Tel Aviv Yaffo (IL)

(73) Assignee: ACERAR LTD., Tel Aviv (IL)

( * ) Notice: Subject to any disclaimer, the term of this patent is extended or adjusted under 35 U.S.C. 154(b) by 813 days.

(21) Appl. No.: 17/615,200

(22) PCT Filed: May 4, 2020

(86) PCT No.: PCT/IL2020/050493
§ 371 (c)(1),
(2) Date: Nov. 30, 2021

(87) PCT Pub. No.: WO2020/240534
PCT Pub. Date: Dec. 3, 2020

(65) Prior Publication Data
US 2022/0230731 A1 Jul. 21, 2022

Related U.S. Application Data

(60) Provisional application No. 62/854,461, filed on May 30, 2019.

(51) Int. Cl.
*G16H 20/70* (2018.01)
*G06N 3/044* (2023.01)
*G06N 3/08* (2023.01)

(52) U.S. Cl.
CPC ............ *G16H 20/70* (2018.01); *G06N 3/044* (2023.01); *G06N 3/08* (2013.01)

(58) Field of Classification Search
CPC ....... G16H 20/70; G06N 3/044; A61B 5/4088
See application file for complete search history.

(56) References Cited

U.S. PATENT DOCUMENTS

| 2013/0266922 A1 | 10/2013 | Needham et al. |
| 2017/0046971 A1 | 2/2017 | Moreno |

(Continued)

FOREIGN PATENT DOCUMENTS

| JP | 2015180933 A | 10/2015 |
| JP | 2016004525 A | 1/2016 |

(Continued)

OTHER PUBLICATIONS

G. Fenza, F. Orciuoli and D. G. Sampson, "Building Adaptive Tutoring Model Using Artificial Neural Networks and Reinforcement Learning, " 2017 IEEE 17th International Conference on Advanced Learning Technologies (ICALT), Timisoara, Romania, 2017, pp. 460-462, doi: 10.1109/ICALT.2017.124. (Year: 2017).*

(Continued)

*Primary Examiner* — Schyler S Sanks
(74) *Attorney, Agent, or Firm* — The Roy Gross Law Firm, LLC; Roy D. Gross

(57) ABSTRACT

Systems and methods of analyzing user feedback in response to a cognition training program, including training at least one machine learning algorithm with a predefined dataset to predict a training success rate, wherein the predefined dataset includes previously received user feedback for users with known characteristics, receiving new user feedback, and determining a prediction of the training success rate with the at least one machine learning algorithm based on the received new user feedback.

19 Claims, 11 Drawing Sheets

(56) References Cited

U.S. PATENT DOCUMENTS

| | | | |
|---|---|---|---|
| 2018/0286272 A1 | 10/2018 | McDermott et al. | |
| 2019/0151654 A1 | 5/2019 | Wingeier et al. | |
| 2019/0231247 A1* | 8/2019 | Bernier | A61B 5/742 |

FOREIGN PATENT DOCUMENTS

| | | |
|---|---|---|
| WO | WO 2018039610 A1 | 3/2018 |
| WO | 2018189549 A1 | 10/2018 |

OTHER PUBLICATIONS

Hausknecht, Matthew, and Peter Stone. "Deep recurrent q-learning for partially observable mdps." 2015 aaai fall symposium series. 2015. (Year: 2015).*

Daisuke Kitakoshi, Ryo Hanada, Keitarou Iwata, Masato Suzuki, Cognitive Training System for Dementia Prevention Using Memory Game Based on the Concept of Human-Agent Interaction, Journal of Advanced Computational Intelligence and Intelligent Informatics, 2015, vol. 19, Issue 6, pp. 727-737 (Year: 2015).*

Song, Xing, S. Q. Xie, and K. C. Aw. "EEG-based brain computer interface for game control." International Conference on Affective Computing and Intelligent Interaction. vol. 20122012. 2012. (Year: 2012).*

Rosch, Jonathan L., and Jennifer J. Vogel-Walcutt. "A review of eye-tracking applications as tools for training." Cognition, technology & work 15 (2013): 313-327 (Year: 2013).*

International Search Report for PCT application No. PCT/IL2020/050493, mailed on Jul. 20, 2020.

Xiang Zhang, Lina Yao, Xianzhi Wang, Jessica Monaghan, David Mcalpine, Yu Zhang. "A Survey on Deep Learning based Brain-Computer Interface: Recent Advances and New Frontiers", vol. 1, No. 1, Article 1. Publication date: Jan. 2018. https://doi.org/10.48550/arXiv.1905.04149.

Fenza et al., "Building Adaptive Tutoring Model using Artificial Neural Networks and Reinforcement Learning", 2017 IEEE 17th International Conference on Advanced Learning Technologies (ICALT), Timisoara, Romania, 2017, pp. 460-462, doi: 10.1109/ICALT.2017.124.

* cited by examiner

```
┌─────────────────────────────────────────────┐
│ Training at least one machine learning      │
│ algorithm with a predefined dataset to predict │
│ a training success rate, wherein the        │
│ predefined dataset comprises previously     │
│ received user feedback for users with known │
│ characteristics                             │
└─────────────────────────────────────────────┘
         ↳ 401
                      ↓
┌─────────────────────────────────────────────┐
│         Receiving new user feedback         │
└─────────────────────────────────────────────┘
         ↳ 402
                      ↓
┌─────────────────────────────────────────────┐
│ Determining a prediction of the training    │
│ success rate with the at least one machine  │
│ learning algorithm based on the received new │
│ user feedback                               │
└─────────────────────────────────────────────┘
         ↳ 403
```

FIG. 4A

Training at least one machine learning algorithm with a predefined dataset to predict a training success rate, wherein the predefined dataset comprises previously received user feedback for users with known characteristics

404

Updating training variables in accordance with the prediction of the training success rate with the at least one machine learning algorithm

405

Receiving new user feedback

```
┌─────────────────────────────────────────────┐
│   Training at least one machine learning    │
│ algorithm with a predefined dataset to predict │
│  a training churn rate, wherein the predefined │
│   dataset comprises previously received user   │
│   feedback for users with known characteristics│
└─────────────────────────────────────────────┘
         │ 501
         ▼
┌─────────────────────────────────────────────┐
│         Receiving new user feedback          │
└─────────────────────────────────────────────┘
         │ 502
         ▼
┌─────────────────────────────────────────────┐
│ Determining a prediction of the training churn │
│ rate with the at least one machine learning    │
│ algorithm based on the received new user       │
│                 feedback                       │
└─────────────────────────────────────────────┘
         503
```

FIG. 5

```
┌─────────────────────────────────────────────┐
│ Training at least one machine learning      │
│ algorithm with a predefined dataset to      │
│ predict cognitive decline,                  │
│ wherein the predefined dataset previously   │
│ received user feedback for users with known │
│ characteristics                             │
└─────────────────────────────────────────────┘
         └─ 601

┌─────────────────────────────────────────────┐
│         Receiving new user feedback         │
└─────────────────────────────────────────────┘
         └─ 602

┌─────────────────────────────────────────────┐
│ Determining a prediction of the cognitive   │
│ decline, with the at least one machine      │
│ learning algorithm based on the received    │
│ new user feedback                           │
└─────────────────────────────────────────────┘
         └─ 603
```

FIG. 6

SYSTEM AND METHOD FOR COGNITIVE TRAINING AND MONITORING

CROSS-REFERENCE TO RELATED APPLICATIONS

This application is a National Phase Application of PCT International Application No. PCT/IL2020/050493, International Filing Date 4 May 2020, claiming the benefit of U.S. Patent Application No. 62/854,461, filed 30 May 2019, all of which are hereby incorporated by reference.

FIELD OF THE INVENTION

The present invention relates to cognitive training. More particularly, the present invention relates to systems and methods for monitoring and analysis of user feedback in response to a cognition training program.

BACKGROUND OF THE INVENTION

People suffering from cognitive problems, or people looking to improve their cognitive skills, sometimes use cognitive training programs in order to improve their cognitive health and train their memory, similar to physical training in a gym. For example, a person can use memory cards, solve a crossword puzzle or sit in front of a computer screen and perform various tasks designed to improve cognitive abilities (such as memory, calculations, vocabulary, etc.).

A major problem with self-administered cognitive training programs (e.g., without any professional supervision) is persistence and/or engagement of the user with the training program. The weekly use can be reduced with time, for example with repetitive programs where the user gradually loses interest in the program and the training result decrease accordingly. In order for any training to be effective people need to continue training for a long period of time. While most people typically begin training with high motivation to improve their cognitive abilities, the average user will not complete the training and may stop or significantly reduce the amount of training sessions over time. Usually, this can happen due to the monotonous training, difficulty understanding how these games are relevant to everyday needs, and/or due to loss of interest. Therefore, current training programs do not make a significant cognitive effect when they are self-administered.

SUMMARY

There is thus provided, in accordance with some embodiments of the invention, a method of analyzing user feedback in response to a cognition training program, including: training, by a processor, at least one machine learning algorithm with a predefined dataset to predict a training success rate, wherein the predefined dataset may include previously received user feedback for users with known characteristics, receiving, by the processor, new user feedback, and determining, by the processor, a prediction of the training success rate with the at least one machine learning algorithm based on the received new user feedback. In some embodiments, the at least one machine learning algorithm may be trained with reinforcement learning.

In some embodiments, a behavioral pattern may be determined from the user feedback. In some embodiments, the at least one machine learning algorithm may be implemented on a recurrent neural network with long short term memory units. In some embodiments, a training churn rate may be predicted. In some embodiments, the received feedback may be monitored for at least one of timing, training session length, training session success rate, attention stability, freeze periods, location, training platform, and number of breaks in the training session.

In some embodiments, the user feedback may be classified to determine a user profile from a list of predefined profiles, wherein the determined prediction of the training success rate may also be based on the determined user profile. In some embodiments, the user profile may be determined based on at least one user characteristic selected from the group consisting of: gender, age, education, location, language, occupation, current occupation status, medical status and marital status. In some embodiments, the user profile may be determined based on clustering of the received feedback and based on at least one user characteristic.

In some embodiments, the user may be monitored with at least one Electroencephalography (EEG) sensor, wherein the cognition training program may be changed based on measured EEG signals. In some embodiments, eye movement of the user may be monitored with at least one imager to determine attention of the user. In some embodiments, a behavioral pattern may be determined from the user feedback, and an alert may be issued when the determined behavioral pattern exceeds a predefined threshold.

There is thus provided, in accordance with some embodiments of the invention, a system for cognitive analyzing of user feedback in response to a cognition training program, including a database including a dataset of previously received user feedback for users with known characteristics, and a processor, coupled to the database and configured to: train at least one machine learning algorithm with the dataset to predict a training success rate, receive new user feedback, and determine a prediction of the training success rate with the at least one machine learning algorithm based on the received new user feedback. In some embodiments, the at least one machine learning algorithm may be trained with reinforced learning.

In some embodiments, the processor may determine a behavioral pattern from the user feedback. In some embodiments, the processor may classify the user feedback to determine a user profile from a list of predefined profiles, wherein the prediction of a training success rate with the at least one machine learning algorithm may also be based on the determined user profile. In some embodiments, the processor may predict a training churn rate with the at least one machine learning algorithm. In some embodiments, the processor may monitor the received feedback for at least one of timing, training session length, training session success rate, attention stability, freeze periods, and number of breaks in the training session.

In some embodiments, the at least one machine learning algorithm may be implemented on a recurrent neural network with long short term memory units. In some embodiments, the user profile may be determined based on at least one user characteristic selected from the group consisting of: gender, age, education, location, language, occupation, current occupation status, and marital status. In some embodiments, the user profile may be determined based on clustering of the received feedback. In some embodiments, at least one Electroencephalography (EEG) sensor may be coupled to the processor, wherein the processor may monitor the user with the at least one EEG sensor, and wherein the user profile may be determined based on measured EEG signals.

In some embodiments, at least one imager may be coupled to the processor, and wherein the processor may monitor eye movement of the user with the at least one imager. In some embodiments, the processor may determine a behavioral pattern from the user feedback and issue an alert when the determined behavioral pattern exceeds a predefined threshold.

There is thus provided, in accordance with some embodiments of the invention, a method of cognitive training, including: determining, by the processor, a behavioral pattern from received user feedback in response to a cognition training program, and correcting, by the processor, the cognition training program with at least one machine learning algorithm based on the determined behavioral pattern in order to improve the cognitive training. In some embodiments, the at least one machine learning algorithm may be trained with previously received user feedback for users with known characteristics.

There is thus provided, in accordance with some embodiments of the invention, a method of analyzing user feedback in response to a cognition training program, including: training, by a processor, at least one machine learning algorithm with a predefined dataset to predict a training success rate, wherein the predefined dataset may include previously received user feedback for users with known characteristics, and updating, by the processor, training variables in accordance with the prediction of the training success rate with the at least one machine learning algorithm. In some embodiments, new user feedback may be received, and the training variables may be re-updated based on the received new user feedback.

There is thus provided, in accordance with some embodiments of the invention, a method of analyzing user feedback in response to a cognition training program, including: training, by a processor, at least one machine learning algorithm with a predefined dataset to predict a training churn rate, wherein the predefined dataset may include previously received user feedback for users with known characteristics, receiving, by the processor, new user feedback, and determining, by the processor, a prediction of the training churn rate with the at least one machine learning algorithm based on the received new user feedback.

There is thus provided, in accordance with some embodiments of the invention, a method of analyzing user feedback in response to a cognition training program, including: training, by a processor, at least one machine learning algorithm with a predefined dataset to predict cognitive decline, wherein the predefined dataset may include previously received user feedback for users with known characteristics, receiving, by the processor, new user feedback, and determining, by the processor, a prediction of the cognitive decline with the at least one machine learning algorithm based on the received new user feedback.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 4A-4B show flowcharts for methods of cognitive analyzing of user feedback in response to a cognition training program, according to some embodiments of the invention;

FIG. 5 shows a flowchart of a method of analyzing user feedback in response to a cognition training program to determine a training churn rate, according to some embodiments of the invention; and FIG. 6 shows a flowchart of a method of analyzing user feedback in response to a cognition training program to determine cognitive decline, according to some embodiments of the invention.

Figure 1:
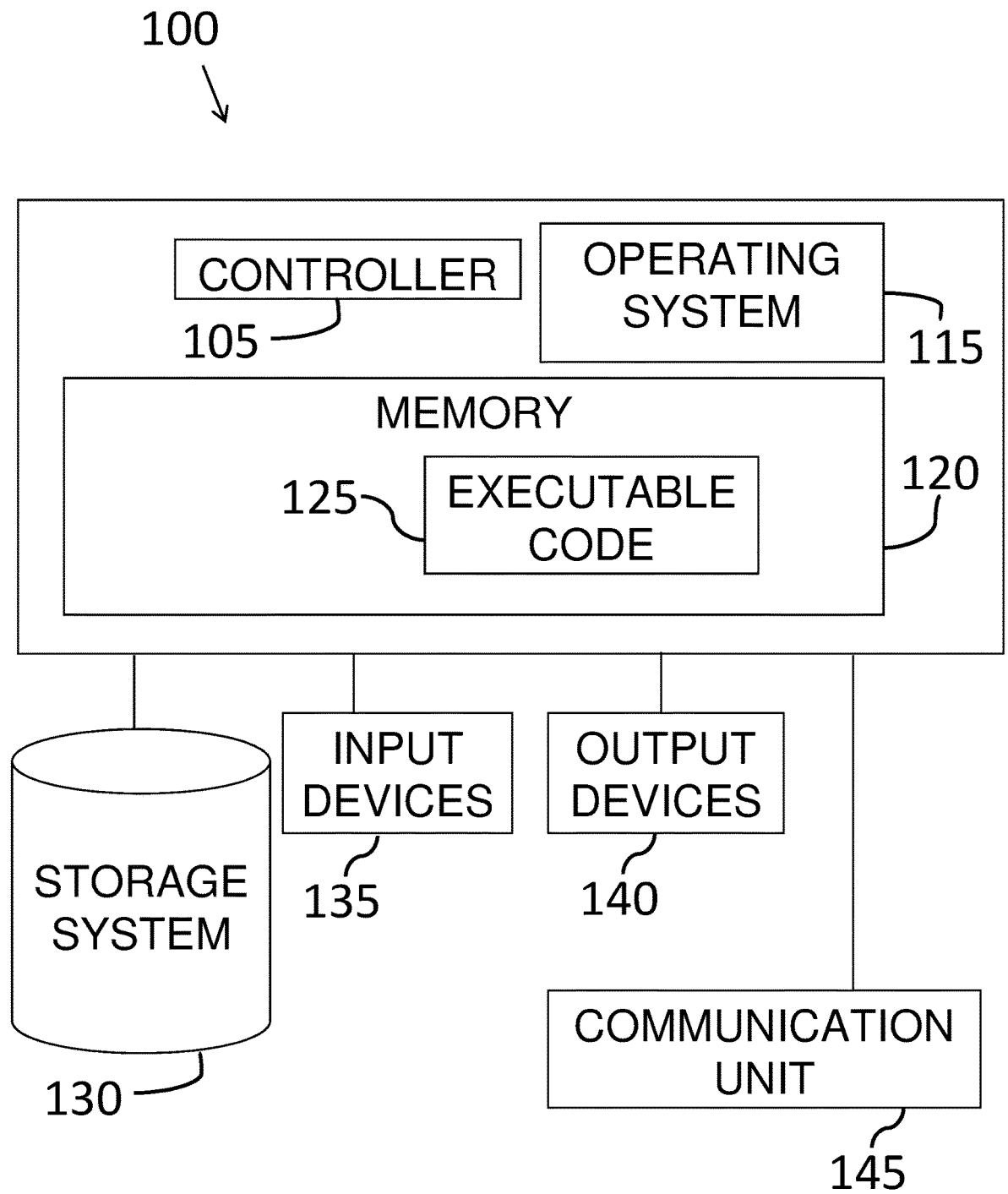
FIG. 1 shows a block diagram of an example computing device, according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF EMBODIMENTS OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing", "computing", "calculating", "determining", "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Reference is made to FIG. 1, which is a schematic block diagram of an example computing device, according to some embodiments of the invention. Computing device 100 may include a controller or processor 105 (e.g., a central processing unit processor (CPU), a chip or any suitable computing or computational device), an operating system 115, memory 120, executable code 125, storage 130, input devices 135 (e.g. a keyboard or touchscreen), and output devices 140 (e.g., a display), a communication unit 145 (e.g., a cellular transmitter or modem, a Wi-Fi communication unit, or the like) for communicating with remote devices via a communication network, such as, for example, the Internet. Controller 105 may be configured to execute program code to perform operations described herein. The system described herein may include one or more computing device(s) 100, for example, to act as the various devices and/or the components shown in FIG. 2A. For example, system 200 may be, or may include computing device 100 or components thereof.

Operating system 115 may be or may include any code segment (e.g., one similar to executable code 125 described herein) designed and/or configured to perform tasks involving coordinating, scheduling, arbitrating, supervising, controlling or otherwise managing operation of computing device 100, for example, scheduling execution of software programs or enabling software programs or other modules or units to communicate.

Memory 120 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 120 may be or may include a plurality of, possibly different memory units. Memory 120 may be a computer or processor non-transitory readable medium, or a computer non-transitory storage medium, e.g., a RAM.

Executable code 125 may be any executable code, e.g., an application, a program, a process, task or script. Executable code 125 may be executed by controller 105 possibly under control of operating system 115. For example, executable code 125 may be a software application that performs methods as further described herein. Although, for the sake of clarity, a single item of executable code 125 is shown in FIG. 1, a system according to embodiments of the invention may include a plurality of executable code segments similar to executable code 125 that may be stored into memory 120 and cause controller 105 to carry out methods described herein.

Storage 130 may be or may include, for example, a hard disk drive, a universal serial bus (USB) device or other suitable removable and/or fixed storage unit. In some embodiments, some of the components shown in FIG. 1 may be omitted. For example, memory 120 may be a non-volatile memory having the storage capacity of storage 130. Accordingly, although shown as a separate component, storage 130 may be embedded or included in memory 120.

Input devices 135 may be or may include a keyboard, a touch screen or pad, one or more sensors or any other or additional suitable input device. Any suitable number of input devices 135 may be operatively connected to computing device 100. Output devices 140 may include one or more displays or monitors and/or any other suitable output devices. Any suitable number of output devices 140 may be operatively connected to computing device 100. Any applicable input/output (I/O) devices may be connected to computing device 100 as shown by blocks 135 and 140. For example, a wired or wireless network interface card (NIC), a universal serial bus (USB) device or external hard drive may be included in input devices 135 and/or output devices 140.

Embodiments of the invention may include an article such as a computer or processor non-transitory readable medium, or a computer or processor non-transitory storage medium, such as for example a memory, a disk drive, or a USB flash memory, encoding, including or storing instructions, e.g., computer-executable instructions, which, when executed by a processor or controller, carry out methods disclosed herein. For example, an article may include a storage medium such as memory 120, computer-executable instructions such as executable code 125 and a controller such as controller 105. Such a non-transitory computer readable medium may be for example a memory, a disk drive, or a USB flash memory, encoding, including or storing instructions, e.g., computer-executable instructions, which when executed by a processor or controller, carry out methods disclosed herein. The storage medium may include, but is not limited to, any type of disk including, semiconductor devices such as read-only memories (ROMs) and/or random access memories (RAMs), flash memories, electrically erasable programmable read-only memories (EEPROMs) or any type of media suitable for storing electronic instructions, including programmable storage devices. For example, in some embodiments, memory 120 is a non-transitory machine-readable medium.

A system according to embodiments of the invention may include components such as, but not limited to, a plurality of central processing units (CPU) or any other suitable multi-purpose or specific processors or controllers (e.g., controllers similar to controller 105), a plurality of input units, a plurality of output units, a plurality of memory units, and a plurality of storage units. A system may additionally include other suitable hardware components and/or software components. In some embodiments, a system may include or may be, for example, a personal computer, a desktop computer, a laptop computer, a workstation, a server computer, a network device, or any other suitable computing device.

According to some embodiments, systems and methods are provided for a personalized computerized cognitive training program configured to support cognitive health in adult users, and specifically memory functions.

Figure 2A:
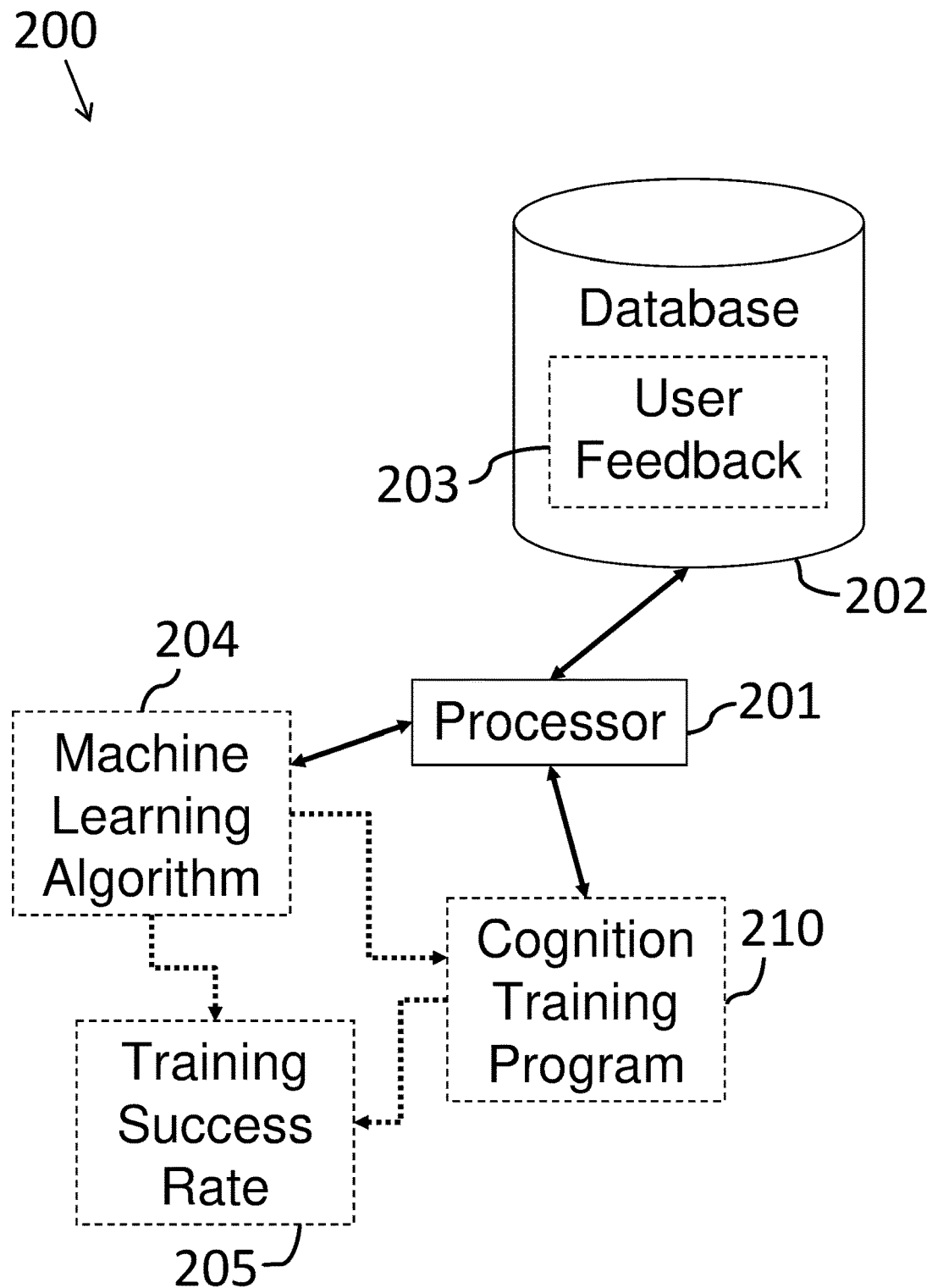
FIGS. 2A-2E show block diagrams of a system for cognitive analyzing of user feedback in response to a cognition training program, according to some embodiments of the invention.

Reference is now made to FIG. 2A, which shows a block diagram of a system 200 for cognitive analyzing of user feedback in response to a cognition training program 210, according to some embodiments. In FIG. 2A, the direction of arrows indicates the direction of information flow, and dashed elements indicate software and/or algorithms.

The system 200 may include at least one processor 201 (such as controller 105, shown in FIG. 1), for example a processor in a mobile device and/or a PC on which the cognition training program 210 may be implemented. The processor 201 may be coupled to a database 202 (such as storage system 130, shown in FIG. 1) including a dataset of previously received user feedback 203 for users with known characteristics. For example, users with known characteristics such as age, gender, medical and/or mental condition, etc., may provide feedback 203 to a cognition training program 210 (e.g., in an initial calibration stage as described in detail herein).

During training, the processor 201 may gather information relating to one or more of the training time of day, training session length, platform used by the user (e.g., PC, tablet, smartphone), and/or training location (e.g., at home or at a public place) in order to improve the cognition training program 210 for future training of that user. In some embodiments, the processor 201 may also gather information from the user feedback 203, such as user response time (e.g., in a game) and/or type of answer (e.g., correct/wrong/missed answer) in different scenarios displayed to the user, and/or target location on the display, and/or type of input (e.g., using keyboard or touchscreen), and/or the number of breaks the users take. In addition to gathering information relating to the type of answer, the processor 201 may also gather information relating to at least one of: success rate, attention stability, lapse of attention, spatial attention, a longest streak (e.g., number of consecutive correct answers in a game), learning curve, sleep quality and/or mood (e.g., determined based on questions in the training sessions or directly from a dedicated device such as a smartwatch or other sensor(s)). In some embodiments, the information gathered by the processor 201 may be stored at the database 202 as user feedback 203.

According to some embodiments, the cognition training program 210 may be modified based on cognitive functioning (e.g., in games, exercises, etc.) identified with low success rate, and/or a high response time standard deviation (e.g., crossing a certain predefined threshold), and/or specific type of mistakes (e.g., location vs. correct identification), etc. The cognitive functions trained may include memory components such as visual perception, feature and object binding, organizing information, semantic networks, attention (crucial for memory processes) and so on. A user's attention may be trained for focus attention, orientation of attention, selective attention, visuo-spacial attention, continuous attention, executive attention and/or attentional control (including, for example, divided attention and inhibition), etc. In some embodiments, the processor 201 may monitor the user feedback 203 to determine training attention based on the overall response time and identifying lapses of attention (e.g., a deviation in a response time) and attention stability (e.g., the response time overall standard deviation size).

The processor 201 may execute at least one machine learning algorithm 204 (e.g., with deep learning using deep neural networks) to train with the dataset of the user feedback 203 and predict a training success rate 205 of a user. The at least one machine learning algorithm 204 may be trained using data previously collected on users while running with predefined rules. In some embodiments, the at least one machine learning algorithm 204 may be trained with supervised training of the computer network using machine learning (e.g., with a neural network). Supervised training may include training with tagged data sets (e.g., with examples of human users training with the system) or include training with supervision of a human operator that tags samples to teach the network. In some embodiments, the at least one machine learning algorithm 204 may be activated for a predefined time period (e.g., semi-automatically) for re-training of the algorithm once a predefined amount of new data is collected. In some embodiments, the at least one machine learning algorithm 204 may be implemented on a recurrent neural network (RNN), for example with long short-term memory (LSTM) units. RNN is a class of artificial neural network where connections between nodes form a directed graph along a temporal sequence. Unlike feedforward neural networks, RNNs with LSTM architecture may have feedback connections to use their internal state (memory) to process sequences of inputs.

In some embodiments, the processor 201 may predict the training success rate 205 (e.g., with supervised learning), where similar users may be identified, for instance from a continuously updated dataset of long-term users based on similar content (e.g., gender, location, age, education, etc.) and/or based on similar behavior (e.g., with respect to the success of their training history). Accordingly, in some embodiments, the training success rate 205 of a particular user may be calculated and/or predicted by the processor 201 based on the success of similar users for a particular training session.

In some embodiments, the cognition training program 210 may receive input from the at least one machine learning algorithm 204 (e.g., directly and/or via processor 201), the input including, e.g., which exercises and/or levels and/or variables to use in order to receive the expected training success rate 205. In some embodiments, the processor 201 may continuously receive user feedback 203 during and/or after training with information for training progress according to the provided instructions, in order to compare the training results with the predicted training success rate 205 in order to constantly improve the at least one machine learning algorithm 204.

In some embodiments, the processor 201 may use the at least one machine learning algorithm 204 (e.g., execute the algorithm to achieve a result) to generate recommendations to increase (or decrease) the training success rate 205. During training, the processor 201 may modify the cognition training program 210 in accordance with the calculate training success rate 205, for instance if the calculated training success rate 205 is below a predefined threshold the cognition training program 210 may be modified to be easier for the user. In some embodiments, the processor 201 may generate statistics (e.g., graphs) to be displayed to the user to reflect which variables affect their cognitive abilities, such as time of training (e.g., time of day or day of the week), sleep quality (e.g., optimized hours of sleep for maximum concentration) and/or if there are differences in training sessions in regard to these variables, etc. In some embodiments, at least some features may be determined by the processor 201 (e.g., success rate or training churn rate) are carried out by different machine learning algorithms.

Figure 2B:
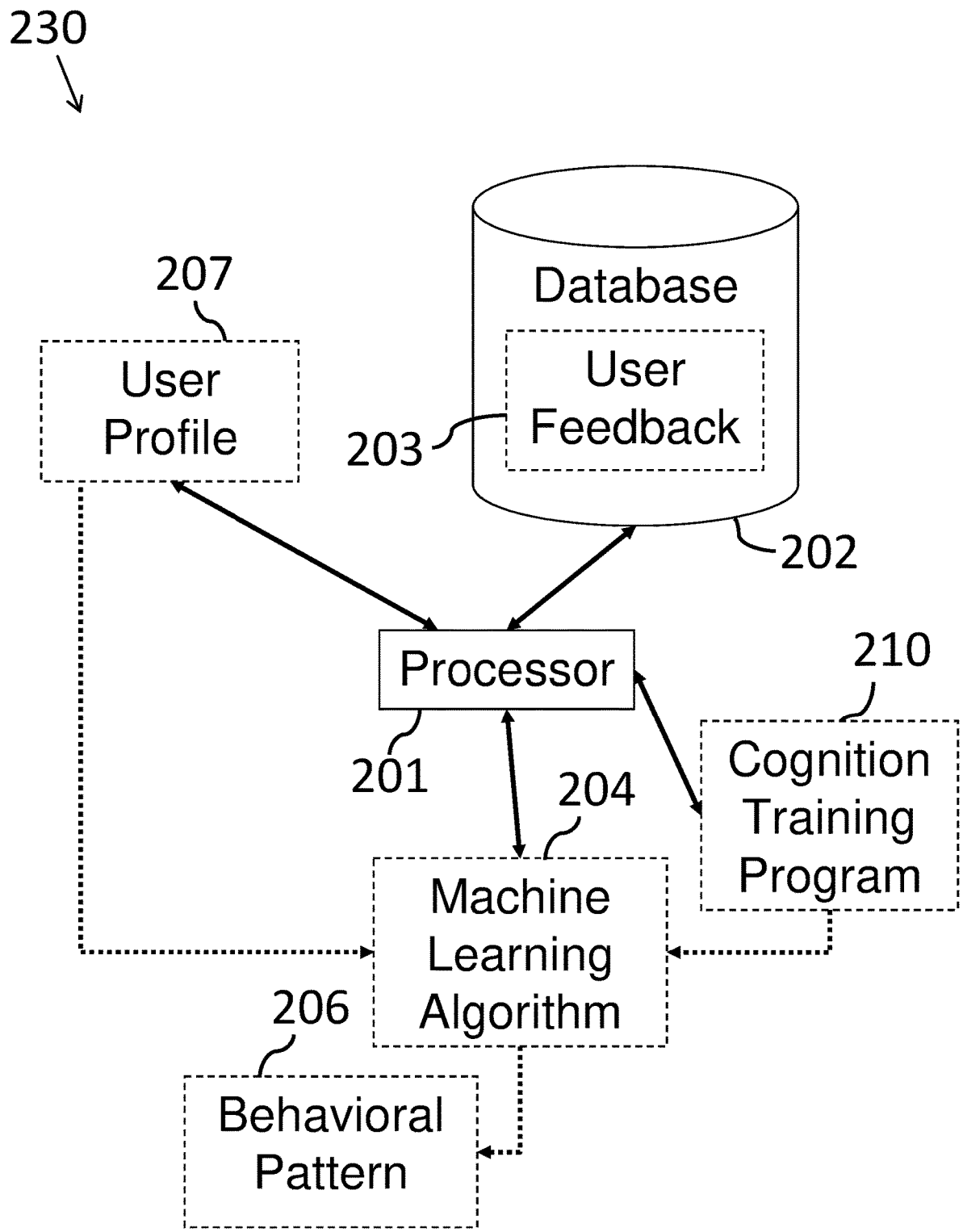
Figure 2C:
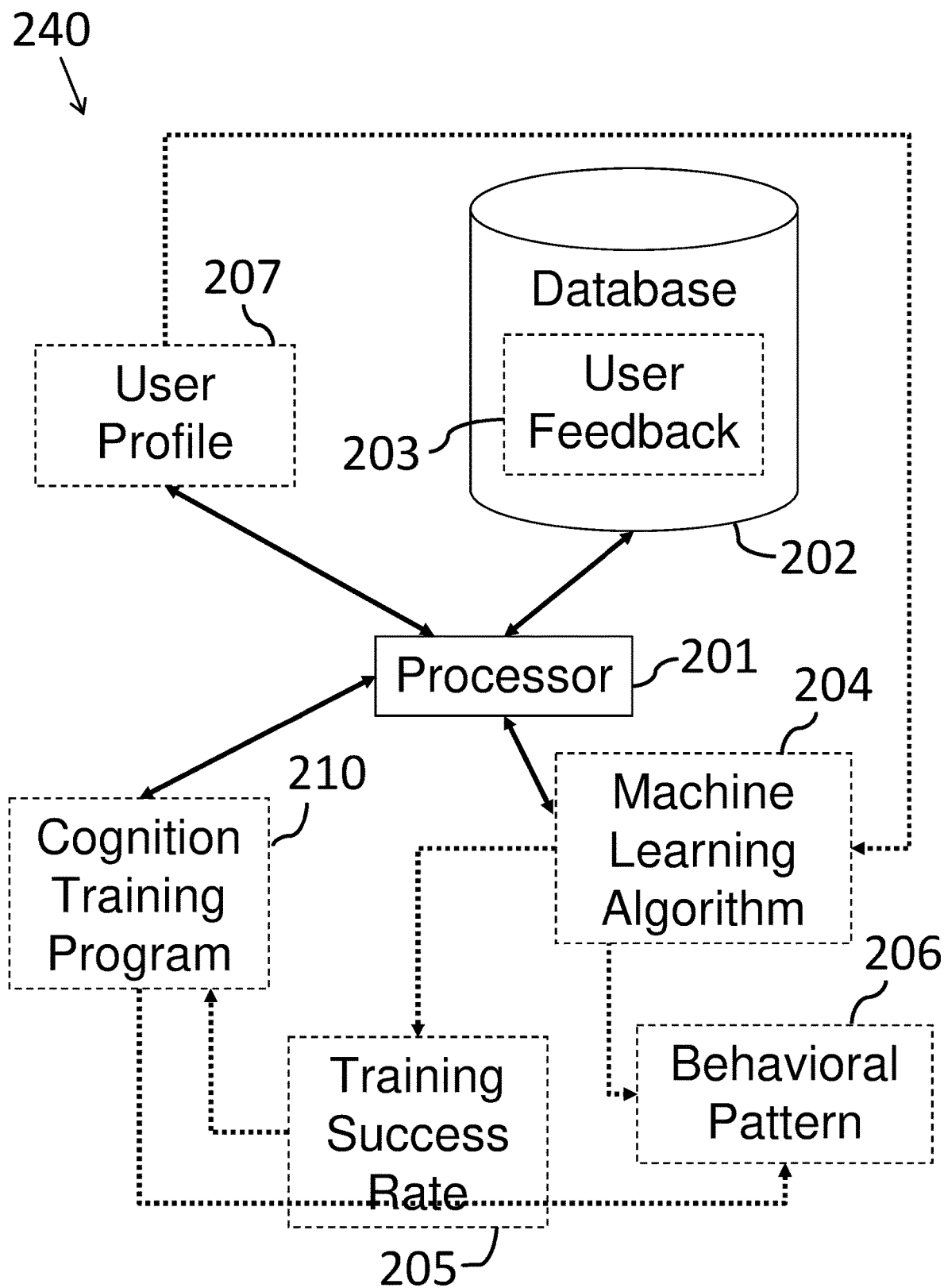

Reference is now made to FIGS. 2B and 2C, which show a block diagram of another system 230 and 240, respectively, for determination of a behavioral pattern 206 in response to a cognition training program 210, according to some embodiments. Some of the elements in FIGS. 2B and 2C may be the same or similar to the elements shown in FIG. 2A, for instance processor 201.

According to some embodiments, the processor 201 may determine a user's behavioral pattern 206 (e.g., a pattern of behavior and/or feedback, such as reaction time and/or correct answers that may reflect cognitive and/or motor abilities) from the user feedback 203, for instance using the machine learning algorithm 204. In some embodiments, the behavioral pattern 206 may be a cognitive behavioral pattern.

The processor 201 may determine a prediction of the training success rate 205 with the at least one machine learning algorithm 204 based on the determined user's behavioral pattern 206 and/or based on user characteristics. In some embodiments, the processor 201 may issue an alert when the determined user's behavioral pattern 206 exceeds a predefined threshold. For example, the machine learning algorithm 204 may compare user's behavior (e.g., from user feedback 203) during training to initial state (e.g., from a user profile 207) in order to determine if the user's behavioral pattern 206 meets or exceeds a predefined threshold such as, for example, determining that the training success rate is reduced by 40%. In some embodiments, the information gathered at the alert procedure may be fed back into the user's behavioral pattern 206 algorithm. For example, the sliding windows technique may be used with supervised learning (e.g., RNN) or unsupervised learning by finding difference between previous windows. For both cases, the distance function between sub-sequences may be defined and used to compute a distance from previous windows as input to several anomaly detection methods.

For example, the machine learning algorithm 204 may be configured to achieve a predefined training success rate 205 (e.g., 80%) for each user, with the training success rate 205 measured, e.g., during the training sessions to keep users training for substantial periods (e.g., if reduced success rate also indicates a reduction in training persistence), and/or the training success rate 205 may be measured in success in completing new levels of the training (such as in a game). When a reduction in success rate 205 is identified, for instance due to a reduction in training time, the machine learning algorithm 204 may be configured to achieve a lower training success rate 205, thereby maintaining training for the user.

In some embodiments, a set of actions for direct interaction with the user may be defined based on certain user's behavioral pattern 206, in order to further increase the training success rate 205 and/or if the user's behavior significantly changed. The user feedback data 203 may be collected with reinforcement and/or supervised learning about the effect of different actions on the user's performance. Based on the collected user feedback data 203, predefined rules and/or the machine learning algorithm may accordingly impose the training and/or the parameters to be presented. For each such action (for instance, initiating a phone call with the user, providing educational material, etc.), the effect on the training success rate 205 may be measured in order to learn which actions improve the training success rate 205. In some embodiments, once the response to the actions is learned by system 200 and/or system 230 and/or system 240, the at least one machine learning algorithm 204 may predict for each user which actions may be required and at what time during training to apply them accordingly.

In some embodiments, the processor 201 may classify the user feedback 203 (and/or processor 201 may instruct an algorithm to perform classification) to determine at least one user profile 207, including age, gender, etc., e.g., from a list of predetermined profiles (e.g., stored at database 202); for instance, at least one profile may be determined by the at least one machine learning algorithm 204. In some embodiments, the determined at least one user profile may be used by at least one of systems 200, 230, 240, 260 and 270 shown in FIGS. 2A-2E. In some embodiments, the determined prediction of the user's behavioral patterns 206 may also be based on the determined at least one user profile 207. In some embodiments, the at least one user profile 207 may be determined also or alternatively based on at least one user characteristic such as gender, age, education, location, language, occupation, current occupation status, medical status and/or marital status. The at least one user profile 207 may also or alternatively be determined based on clustering of the received feedback.

Figure 2D:
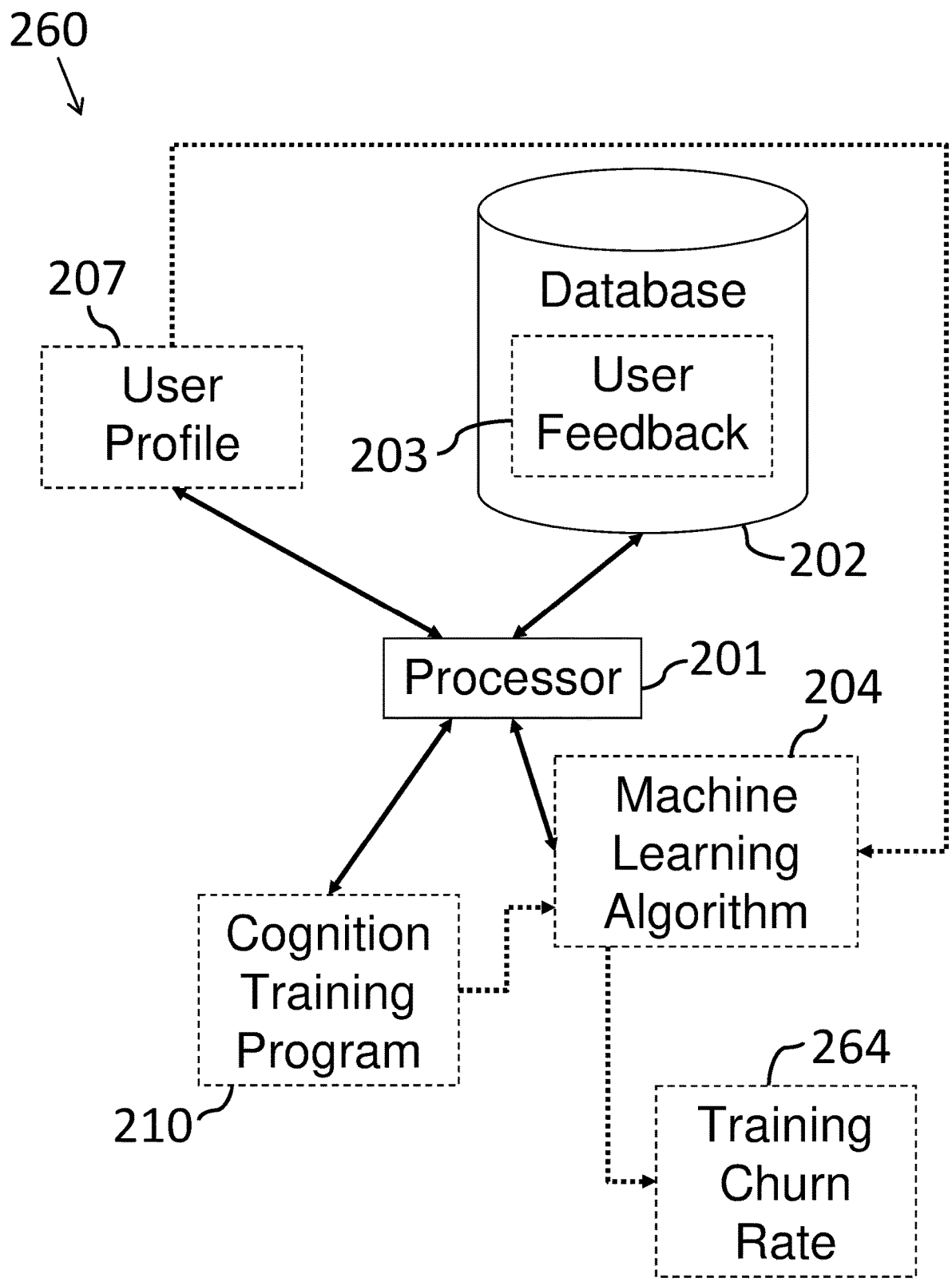

Reference is now made to FIG. 2D, which shows a block diagram of another system 260 for determination of a training churn rate 264 in response to a cognition training program 210, according to some embodiments. Some of the elements in the FIG. 2D may be the same or similar to the elements shown in FIG. 2A, for instance processor 201.

According to some embodiments, the processor 201 may predict a training churn rate 264 with the machine learning algorithm 204. A user training churn rate may be defined with different levels of ongoing engagement (e.g., based on training duration and/or time of day of training).

In some embodiments, data of ongoing use and/or user engagement may be collected (e.g., if a user closed an account or stopped training) so as to predict, using the machine learning algorithm 204, the users training habits and/or expected training churn rate 264. In some embodiments, the machine learning algorithm 204 may receive as input data of other users previously identified with reduced engagement and/or stopped training all together to be compared with collected new training data of the user in order to predict the expected training churn rate 264, for example also based on the user profile 207.

According to some embodiments, the processor 201 may detect changes and/or anomalies in a user's behavior, for instance with unsupervised learning. The processor 201 may monitor user performance and define a profile per user, with an expected behavior for each profile. In some embodiments, non-trivial or significant deviation (e.g., predefined prior to training) from the expected behavior detected in a new training session may be flagged to raise an alert, for example to initiate contact with the user (e.g., a phone call to the user to try and understand the cause of the anomaly, or if there is a medical problem or a major change such as grief, etc.).

In some embodiments, measurements of the user behavior may be performed at predefined intervals, e.g., once a month, as an objective measure or assessment to see if there is any change in the cognitive abilities.

In some embodiments, the machine learning algorithm 204 may receive as input data for the user's behavioral patterns 206 (shown in FIG. 2C) in order to determine change in behavior, for example to determine the training churn rate 264.

Figure 2E:
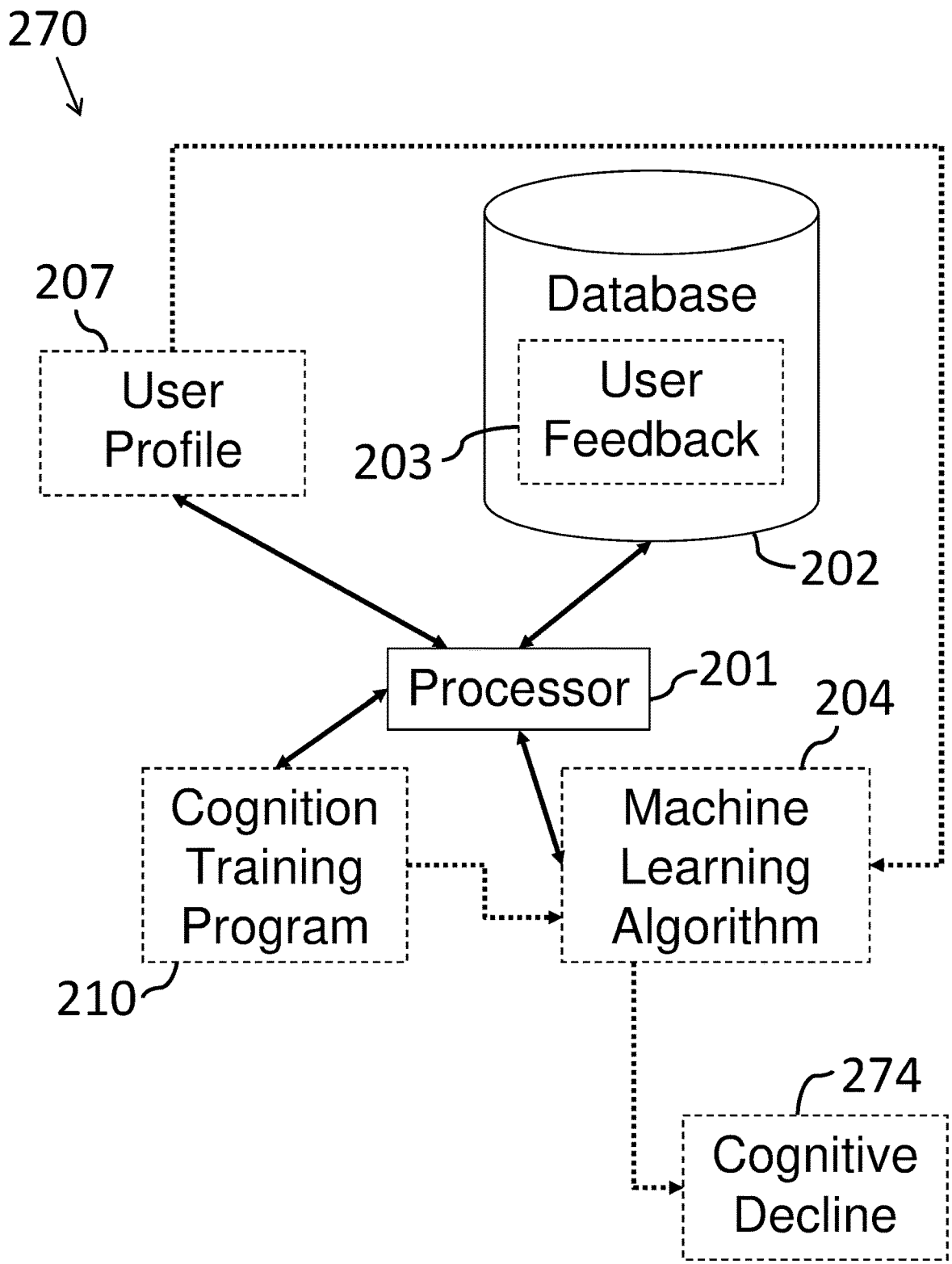

Reference is now made to FIG. 2E, which shows a block diagram of another system 270, for determination of cognitive decline 274 in response to a cognition training program 210, according to some embodiments. Some of the elements in the FIG. 2E may be the same or similar to the elements shown in FIG. 2A, for instance processor 201.

In some embodiments, the processor 201 may predict and/or detect cognitive decline 274 with the machine learning algorithm 204, related to mild cognitive impairment (MCI). MCI may cause a noticeable and measurable decline in cognitive abilities, including memory and thinking skills (judgment, sound decision making, etc.). A person with MCI is at an increased risk of developing Alzheimer's or another type of dementia.

In some embodiments, if users that have different stages of MCI are initially tagged, for instance by diagnosis of an external medical authority, the at least one machine learning algorithm 204 may learn behavioral patterns for such users, e.g., in order to later identify similar patterns for users that are not tagged at some stage of MCI. Thus, prediction of MCI may be available by system 200 and/or system 270. In some embodiments, a multi-label time series may be used with minority class prediction algorithm (for new users), e.g. with an attention mechanism or LSTM. Over sampling or Generative Adversarial Networks (GANs) mechanisms may be used to enhance the set of examples. In some embodiments, unsupervised detection may be used with a cluster based algorithm such as Local Outlier Factor (LOF), Kernel Density Estimation (KDE) or K-Means to identify the MCI level of the users.

In some embodiments, the machine learning algorithm 204 may receive as input data of other users previously identified with cognitive decline (e.g., with MCI or dementia) to be compared with collected new training data of the user, e.g., in order to predict the expected cognitive decline 274, for example may also be based on the user profile 207.

In some embodiments, the machine learning algorithm 204 may receive as input data for the user's behavioral patterns 206 (shown in FIG. 2C) in order to determine change in behavior, for example to determine cognitive decline 274.

Figure 3:
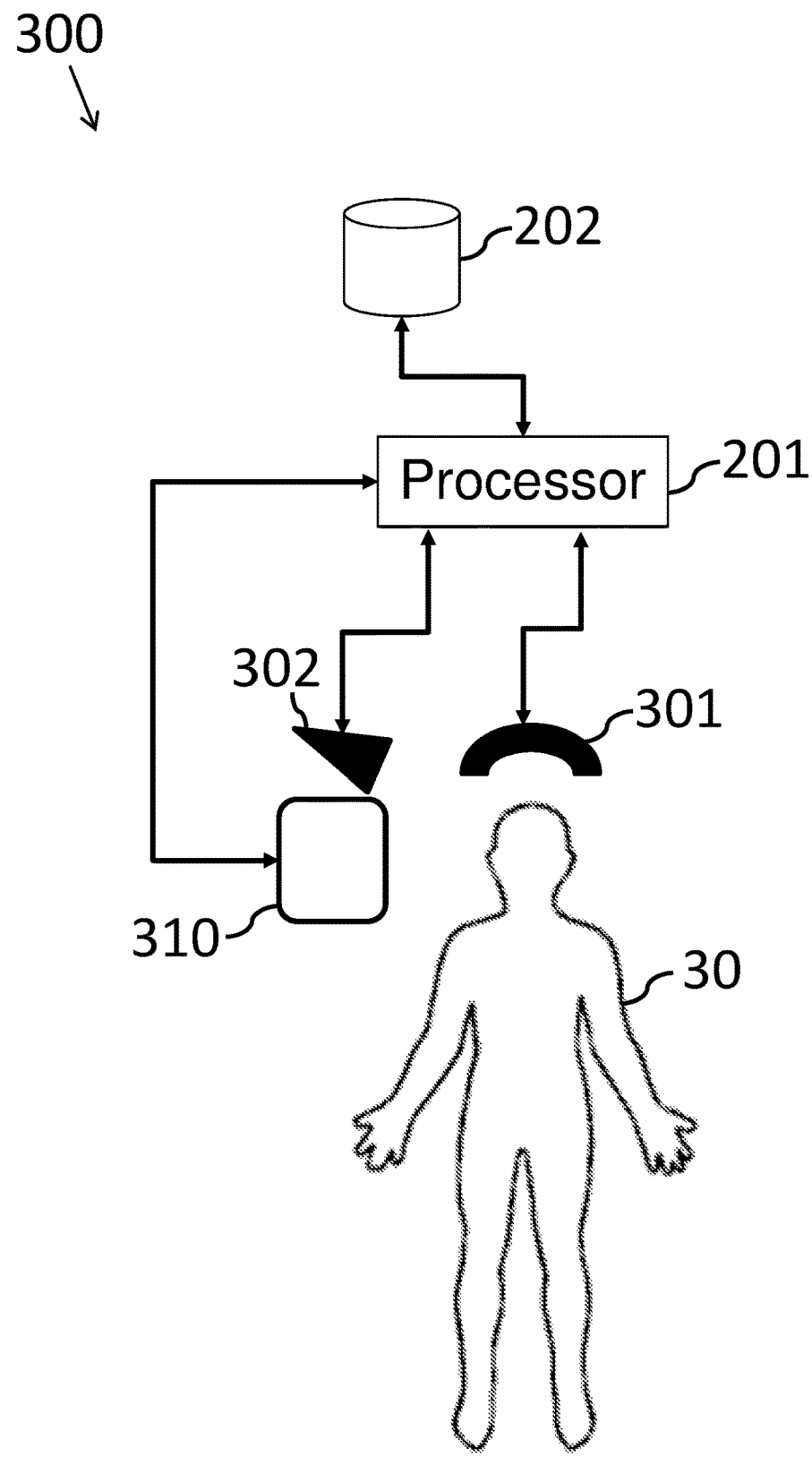
FIG. 3 shows a block diagram of a system for cognitive data collection, according to some embodiments of the invention.

Reference is now made to FIG. 3, which shows a block diagram of a system 300 for cognitive data collection, according to some embodiments. In some embodiments, system 300 may also include some or all elements of system 200 (such as processor 201 and database 202) with the elements of system 300 added in order to collect cognitive data from user 30.

In some embodiments, the system 300 may include at least one Electroencephalography (EEG) sensor 301, to measure EEG signals, coupled to the processor 201, the processor 201 being configured to monitor cognitive signals of the user 30 with the at least one EEG sensor 301. In some embodiments, the user profile 207 may also be determined based on the measured EEG signals. For example, the user 30 may wear a headset with the at least one EEG sensor 301 to collect measurements on brain waves and specific activities using commercial EEG channels (1-16) or clinical EEG channels (16-64), depending for private use or admitted by a clinician, respectively. In some embodiments, the determined training success rate 205 may be refined based on data collected by the at least one EEG sensor 301.

In some embodiments, the EEG sensor 301 may be used similarly to provide neurofeedback, following different brain waves (e.g., alpha, beta, theta) and the relations between them, for instance to find correlation between the brain waves in response to the cognition training program 210. In some embodiments, the measured signals may be integrated into the training session (e.g., into games), with a specific response to measured waves and/or wave relation thresholds. In some embodiments, the training may also include an option for a dual task with neurofeedback based on brain wave activity (e.g., based on alpha level or theta/beta levels) and predefined levels and/or measures to maintain while training.

In some embodiments, the system 300 may include at least one imager 302, e.g., coupled to the processor 201, the processor 201 configured to monitor eye movement of the user 30 for content displayed on display 310 with the at least one imager 302, and accordingly determine concentration and/or attention of the user 30 during training. In some embodiments, the determined training success rate 205 may be refined, e.g., based on data collected by the at least one imager 302.

In some embodiments, the at least one imager 302 may track eye movement and/or pupil size with a camera of a computerized device (such as computing device 100 shown in FIG. 1), for instance a tablet, smartphone, etc. or by a clinical eye tracker. The eye tracking data may be collected during training and in relation to the state presented in the training display 310. In some embodiments, the processor 201 may analyze the gathered eye tracking data to identify saccades, fixations, pupil size, etc., to be correlated with content presented on display 310 to determine attention quality, attention measures and memory measures.

In some embodiments, at least some training sessions may be carried out in a virtual reality environment. For instance, a wearable single device (e.g., a headset) may include the EEG sensor 301 and/or the imager 302 and/or virtual reality imaging displayed with the headset, to combine biofeedback with pulse rate and sweat monitoring.

In some embodiments, the processor 201 may perform analysis on data gathered from external devices (such as EEG sensor 301 and/or imager 302) as well as other external devices used by the user such as activity trackers, smartwatch, smartphone, clinical data, and testing results to improve the cognition training program 210 and increase the training success rate 205 accordingly. The additional gathered data may relate to sleep quality, daily activity, location (e.g., using GPS data), stability (e.g., hand stability while holding the device), and/or emotional status (e.g., based on voice and speech recognition, and/or based on nourishment, medications, etc.). In some embodiments, this gathered data may be computed using the at least one machine learning algorithm 204, e.g., to provide more accurate personalized training, personal recommendations and/or cognitive flagging.

According to some embodiments, the processor 201 may calculate the training success rate 205 and/or general training progress based on correct answer percentage and/or response time, as well as based on spatial attention detection, e.g., to measure how the user divides the attention in the surrounding space. Accordingly, in some embodiments, the training may include targets in different areas of the display 310 and the received responses (e.g., registered as the user feedback 203) between those areas may be compared, for example, to create a spatial attention map and locate areas of "neglect" (within the display area). These areas may be marked and trained in order to improve the user's spatial attention.

Reference is now made to FIG. 4A, which shows a flowchart of a method of analyzing user feedback 203 in response to a cognition training program 210, according to some embodiments.

The at least one machine learning algorithm 204 may be trained at step 401 (e.g., by processor 201) with a predefined dataset to predict a training success rate 205, in which the predefined dataset may include previously received user feedback for users with known characteristics. New user feedback may be received at step 402, and a prediction of the training success rate 205 may be determined at step 403 (e.g., by processor 201) using the at least one machine learning algorithm 204 based on the received new user feedback. In some embodiments, the at least one machine learning algorithm 204 may be trained with reinforcement learning. In some embodiments, transfer learning algorithms may be used in order to use data of healthy people to build a prediction model of people with a cognitive decline.

Reference is now made to FIG. 4B, which shows a flowchart of a method of analyzing user feedback 203 in response to a cognition training program 210, according to some embodiments. In some embodiments, at step 404, the at least one machine learning algorithm 204 may be trained (e.g., by processor 201) with a predefined dataset to predict a training success rate 205, in which the predefined dataset may include previously received user feedback for users with known characteristics. A training set and/or the training variables may be determined to meet prediction of the training success rate 205 (e.g., with a predetermined threshold) where the training variables may be updated at step 405 in accordance with the prediction of the training success rate with the at least one machine learning algorithm 204. When new user feedback is received at step 406, the training variables may be updated at step 405 again.

According to some embodiments, the at least one machine learning algorithm 204 may be trained (e.g., by the processor 201) with a predefined dataset, e.g., to determine a user's behavioral pattern 206, in which the predefined dataset may include previously received user feedback for users with known characteristics as well as previously calculated behavioral pattern of other users. In some embodiments, new user feedback may be received, and a comparison of the user's behavioral pattern 206 to the new received data may be carried out (e.g., by the processor 201) with the at least one machine learning algorithm 204 to identify anomalies in the behavioral pattern 206.

According to some embodiments, the at least one machine learning algorithm 204 may be trained (e.g., by the processor 201) with a predefined dataset, e.g., to determine a user's behavioral pattern 206, in which the predefined dataset may include previously received user feedback for users with known characteristics as well as previously calculated behavioral pattern of other users. The at least one machine learning algorithm 204 may be trained to accordingly predict the user's behavior in other situations, such as prediction of behavior under stressful conditions for a particular user.

Reference is now made to FIG. 5, which shows a flowchart of a method of analyzing user feedback 203 in response to a cognition training program 210 to determine a training churn rate 264, according to some embodiments.

In some embodiments, the at least one machine learning algorithm 204 may be trained at step 501 (e.g., by the processor 201) with a predefined dataset to predict a training churn rate 264, in which the predefined dataset may include previously received user feedback for users with known characteristics (e.g., user feedback for number of training sessions, training frequency, training time/date etc.). New user feedback may be received at step 502, and a prediction of the training churn rate 264 may be determined at step 503 (e.g., by processor 201) with the at least one machine learning algorithm 204 based on the received new user feedback.

Reference is now made to FIG. 6, which shows a flowchart of a method of analyzing user feedback 203 in response to a cognition training program 210 to determine cognitive decline 274, according to some embodiments.

In some embodiments, the at least one machine learning algorithm 204 may be trained at step 601 (e.g., by processor 201) with a predefined dataset to flag possible cognitive decline and/or predict cognitive decline 274, in which the predefined dataset may include previously received user feedback for users with known characteristics. The predefined dataset may include previously calculated patterns that characterize different cognitive deterioration states, for instance based on previously received user feedback for users with known characteristics including cognitive clinical diagnosis. New user feedback may be received at step 602, and a prediction of the cognitive decline 274 may be determined at step 603 (e.g., by processor 201) with the at least one machine learning algorithm 204 based on the received new user feedback.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

Various embodiments have been presented. Each of these embodiments may of course include features from other embodiments presented, and embodiments not specifically described may include various features described herein.

The invention claimed is:

1. A method of analyzing user feedback in response to a cognition training program, the method comprising:
training, by a processor, at least one machine learning algorithm with a predefined dataset to predict a training success rate of a particular user, wherein the predefined dataset comprises previously received user feedback for users with known characteristics, said feedback representing a user response to a displayed scenario;
receiving, by the processor, new user feedback representing a new user response to the displayed scenario;
determining, by the processor, a prediction of a training success rate of the new user with the at least one machine learning algorithm based on the received new user feedback;
modifying, by the processor, the cognition training program in accordance with the predicted training success rate of the new user;
iteratively retraining the at least one machine learning algorithm with the received new user feedback to improve prediction of the training success rate, using reinforcement learning;
determining, by the processor, a behavior pattern of the new user in response to the modified cognition training program;
determining, by the processor, reduction of the training success rate, based on the determined behavior pattern; and
issuing an alert indicating cognitive decline, when the reduction of the training success rate exceeds a predefined threshold.

2. The method of claim 1, further comprising determining, by the processor, a behavioral pattern from the user feedback.

3. The method of claim 1, wherein the at least one machine learning algorithm is implemented on a recurrent neural network with long short term memory units.

4. The method of claim 1, further comprising predicting, by the processor, a training churn rate.

5. The method of claim 1, further comprising monitoring, by the processor, the received feedback for at least one of timing, training session length, training session success rate, attention stability, freeze periods, location, training platform, and number of breaks in the training session.

6. The method of claim 1, further comprising classifying, by the processor, the user feedback to determine a user profile from a list of predefined profiles, wherein the determined prediction of the training success rate is also based on the determined user profile.

7. The method of claim 6, wherein the user profile is further determined based on at least one user characteristic selected from the group consisting of: gender, age, education, location, language, occupation, current occupation status, medical status and marital status.

8. The method of claim 7, wherein the user profile is further determined based on clustering of the received feedback and based on the at least one user characteristic.

9. The method of claim 1, further comprising monitoring, by the processor, the user with at least one Electroencephalography (EEG) sensor, wherein the cognition training program is changed based on measured EEG signals.

10. The method of claim 1, further comprising monitoring, by the processor, eye movement of the user with at least one imager to determine attention of the user.

11. A system for cognitive analyzing of user feedback in response to a cognition training program, the system comprising:

a database comprising a dataset of previously received user feedback for users with known characteristics; and a processor, coupled to the database and configured to:

train at least one machine learning algorithm with the dataset to predict a training success rate;

receive new user feedback;

determine a prediction of the training success rate of the new user with the at least one machine learning algorithm based on the received new user feedback;

modify the cognition training program in accordance with the predicted training success rate of the new user;

iteratively retrain the at least one machine learning algorithm with the received new user feedback to improve prediction of the training success rate, using reinforcement learning;

determine a behavioral pattern of the new user in response to the modified cognition training program;

determine a reduction in the training success rate based on the determined behavioral pattern; and issue an alert indicating cognitive decline when the determined reduction in the training success rate exceeds a predefined threshold.

12. The system of claim 11, wherein the processor is further configured to determine a behavioral pattern from the user feedback.

13. The system of claim 11, wherein the processor is further configured to classify the user feedback to determine a user profile from a list of predefined profiles, wherein the prediction of a training success rate with the at least one machine learning algorithm is also based on the determined user profile.

14. The system of claim 11, wherein the at least one machine learning algorithm is implemented on a recurrent neural network with long short term memory units.

15. The system of claim 11, wherein the processor is further configured to predict a training churn rate with the at least one machine learning algorithm.

16. The system of claim 11, wherein the processor is further configured to monitor the received feedback for at least one of timing, training session length, training session success rate, attention stability, freeze periods, and number of breaks in the training session.

17. The system of claim 13, wherein the user profile is further determined based on at least one user characteristic selected from the group consisting of: gender, age, education, location, language, occupation, current occupation status, and marital status.

18. The system of claim 13, further comprising at least one Electroencephalography (EEG) sensor coupled to the processor, wherein the processor is further configured to monitor the user with the at least one EEG sensor, and wherein the user profile is determined based on measured EEG signals.

19. The system of claim 11, further comprising at least one imager coupled to the processor, and wherein the processor is further configured to monitor eye movement of the user with the at least one imager.

* * * * *